United States Patent [19]

Carnahan et al.

[11] Patent Number: 5,723,861
[45] Date of Patent: Mar. 3, 1998

[54] RECIRCULATING FILTRATION SYSTEM FOR USE WITH A TRANSPORTABLE ION MOBILITY SPECTROMETER

[75] Inventors: Byron Lee Carnahan, Pittsburgh; Alexander Semenovich Tarassov, Mars, both of Pa.

[73] Assignee: Mine Safety Appliances Company, Pittsburgh, Pa.

[21] Appl. No.: 628,147

[22] Filed: Apr. 4, 1996

[51] Int. Cl.$^6$ .............................. H01J 49/40; H01J 49/04
[52] U.S. Cl. ................................. 250/287; 250/288
[58] Field of Search ............................ 250/287, 288

[56] References Cited

U.S. PATENT DOCUMENTS

| | | | |
|---|---|---|---|
| 3,668,382 | 6/1972 | Cohen et al. | 250/287 |
| 4,317,995 | 3/1982 | Bradshaw et al. | 250/288 |
| 5,420,424 | 5/1995 | Carnahan et al. | 250/287 |

Primary Examiner—Jack I. Berman
Attorney, Agent, or Firm—Titus & McConomy

[57] ABSTRACT

Generally, the present invention provides a recirculating filtration system for use with a transportable ion mobility spectrometer. One preferred embodiment of the transportable recirculating filtration system comprises a pump connected with a set of filters and flow sensors to an ion mobility spectrometry (IMS) sensor. The IMS sensor's outlet flow is cleaned by the filters and recirculated by the pump back into the IMS sensor as the carrier fluid stream flow. A portion of the IMS sensor's outlet flow equal to the amount of flow introduced into the sensor is exhausted from the filtration system to maintain a constant total flow volume through the system as the sample is being taken. An alternate preferred embodiment of the present invention provides a transportable recirculating filtration system for measuring an unknown concentration of a selected ionizable contaminant substance such as benzene present in a sample fluid stream in which other substances may coexist. The filtration system of the alternate preferred embodiment comprises a pump connected with a set of filters, flow sensors, and a plurality of valves to a device for introducing a controlled concentration of the selected ionizable contaminant into an ion mobility spectrometry (IMS) sensor. The unknown concentration is calculated using the Standard Addition Method. The alternate preferred embodiment of the present invention also provides a recirculating filtration system which can be used to calibrate the IMS sensor by establishing which ionogram structures result from the presence of a particular analyte in the sample stream. A known concentration of an analyte is introduced into the sample stream. The resulting ionogram is compared to an ionogram recorded with no contaminants present. By comparing these spectra, a correlation can be made between the positions of features in the ionogram and the analyte which gives rise to these features.

20 Claims, 2 Drawing Sheets

– 1 –

RECIRCULATING FILTRATION SYSTEM FOR USE WITH A TRANSPORTABLE ION MOBILITY SPECTROMETER

FIELD OF THE INVENTION

The invention relates generally to transportable recirculating filtration systems for use in conducting measurements with an ion mobility spectrometer (IMS), and specifically to a transportable recirculating filtration system for use with a field IMS sensor.

BACKGROUND OF THE INVENTION

U.S. Pat. No. 5,420,424 provides a sensor using ion mobility spectrometry (IMS) to detect trace concentration level species present in a sample gas stream. The IMS sensor disclosed in U.S. Pat. No. 5,420,424 utilizes periodic electrical fields to separate different species of ions according to the functional dependence of their mobility with electric field strength. Ions generated in the ionization chamber of the IMS sensor are guided through an ion filter to an ion detector by an electric field known as the "dispersion field." This "dispersion field" is created by an asymmetric periodic radio frequency (RF) voltage applied between a pair of closely spaced longitudinal electrodes. The displacement of the ions induced by the dispersion field is modified or compensated by a second electric field known as the "compensation field." The compensation field is created by an adjustable time independent direct current electrical potential that is applied between the electrodes to isolate a particular ion species for detection as a result of the variance in mobility between particular ion species as a function of electric field strength. This form of ion mobility spectrometry, known as field ion spectrometry (FIS), offers a new method of detecting species present at trace (parts per million to parts per trillion) concentration levels in a sample gas to be analyzed.

To avoid compromising the sensor's performance due to impurities which may be present in the carrier fluid stream that transports the ions through the ion filter, existing IMS sensor designs require connection to a filtration system to clean the carrier fluid stream flow prior to its introduction into the sensor. The use of a stationary filtration source presents a problem if the IMS sensor is to be used as a portable instrument in the detection of atmospheric contaminants in remote locations. Existing portable filtration systems used with IMS devices are not compatible with the IMS design disclosed in U.S. Pat. No. 5,420,424. The present invention solves this problem by providing a recirculating filtration system for use with a transportable IMS sensor of the design disclosed in U.S. Pat. No. 5,420,424.

An alternate preferred embodiment of the present invention provides a recirculating filtration system configuration for use with a transportable IMS sensor that permits use of the Standard Addition Method in the IMS measurement of the concentration level of the contaminant of interest being sampled. The ambient air sample containing the contaminant of interest can compromise IMS performance due to the variable amount of humidity and trace species present in the ambient air stream. The accuracy of the sensor's concentration measurement can be adversely affected by charge transfer reactions which occur between the ionizable contaminant of interest and other ionizable species present in the ambient air sample. Charge transfer reactions can either enhance or diminish the net efficiency with which the contaminant of interest is ionized. Consequently, the sensor's apparent response would depend not only on the concentration of the contaminant of interest in the ambient air sample, but also on the concentration of other substances which contribute to its ionization through these charge transfer reactions. The adverse effects of charge transfer reactions on the IMS sensor's performance can be eliminated through the use of a filtration system configuration which introduces a known concentration of the ionizable contaminant of interest into a fluid stream containing an unknown concentration of the selected contaminant. This permits utilization of a measurement technique known as the Standard Addition Method to quantify the unknown concentration. The Standard Addition Method compares the IMS measurement of the unknown concentration level to the known concentration level in a manner that eliminates the effects of charge transfer reactions on the result.

Accordingly, one embodiment of the present invention preferably provides a recirculating filtration system for use with a transportable ion mobility spectrometry (IMS) sensor. An alternate embodiment of the present invention preferably provides a recirculating filtration system for use with a transportable IMS sensor in measuring an unknown concentration of a selected ionizable contaminant substance present in a sample in which other substances may coexist.

Preferably, the alternate embodiment of the present invention provides a recirculating filtration system which permits use of the Standard Addition Method with an IMS sensor to make a quantitative measurements of an unknown concentration of the selected contaminant. Preferably, the alternate embodiment of the present invention also provides a method of using the recirculating filtration system for comparing the unknown concentration of the selected contaminant to a known concentration level of that contaminant in a manner that corrects for the effects of charge transfer reactions on the result.

The alternate preferred embodiment of the present invention also provides a recirculating filtration system which can be used to calibrate the IMS sensor by establishing which ionogram structures result from the presence of a particular analyte in the sample stream. A known concentration of an analyte is introduced into the sample stream. The resulting ionogram is compared to an ionogram recorded with no contaminants present. By comparing these spectra, a correlation can be made between the positions of features in the ionogram and the analyte which gives rise to these features.

SUMMARY OF THE INVENTION

Generally, the present invention provides a recirculating filtration system for use with a transportable ion mobility spectrometer. One preferred embodiment of the transportable recirculating filtration system comprises a pump connected with a set of filters and flow sensors to an ion mobility spectrometry (IMS) sensor preferably of the design disclosed in U.S. Pat. No. 5,420,424. The IMS sensor's outer flow is cleaned by the filters and recirculated by the pump back into the IMS sensor as the carrier fluid stream flow. A portion of the IMS sensor's outlet flow equal to the amount of flow introduced into the sensor is exhausted from the filtration system to maintain a constant total flow volume through the system as the sample is being taken.

An alternate preferred embodiment of the present invention provides a transportable recirculating filtration system for measuring an unknown concentration of a selected ionizable contaminant substance such as benzene present in a sample fluid stream in which other substances may coexist. The filtration system of the alternate preferred embodiment comprises a pump connected with a set of filters, flow sensors, and a plurality of valves to a device for introducing a controlled concentration of the selected ionizable contaminant into an ion mobility spectrometry (IMS) sensor preferably of the design disclosed in U.S. Pat. No. 5,420,424.

The measurement of an unknown concentration of the selected contaminant preferably comprises the following steps: (1) combining the controlled contaminant concentration with an unknown concentration of the same contaminant to measure the IMS sensor's response to the combined controlled and unknown concentrations; (2) measuring the IMS sensor's response to only the unknown concentration; and (3) determining this unknown concentration by comparing the measurement in step (1) to the measurement in step (2).

The alternate preferred embodiment of the present invention also provides a recirculating filtration system which can be used to calibrate the IMS sensor by establishing which ionogram structures result from the presence of a particular analyte in the sample stream. A known concentration of an analyte is introduced into the sample stream. The resulting ionogram is compared to an ionogram recorded with no contaminants present. By comparing these spectra, a correlation can be made between the positions of features in the ionogram and the analyte which gives rise to these features.

Other details, objects, and advantages of the present invention will become apparent in the following description of the presently preferred embodiments.

BRIEF DESCRIPTION OF THE DETAILED DRAWINGS

In the accompanying drawings, the preferred embodiments of the present invention and preferred methods of practicing the present invention are illustrated wherein:

FIG. 1 is a schematic fluid system diagram of a preferred embodiment of the present invention which provides a recirculating filtration system for use with a transportable IMS sensor; and FIG. 2 is a schematic fluid system diagram of an alternate preferred embodiment of the present invention providing a portable recirculating filtration system for measuring an unknown concentration of a selected ionizable contaminant substance when present in a sample fluid stream in which other substances may coexist.

DETAILED DESCRIPTION OF THE PREFERRED EMBODIMENT

Figure 1:
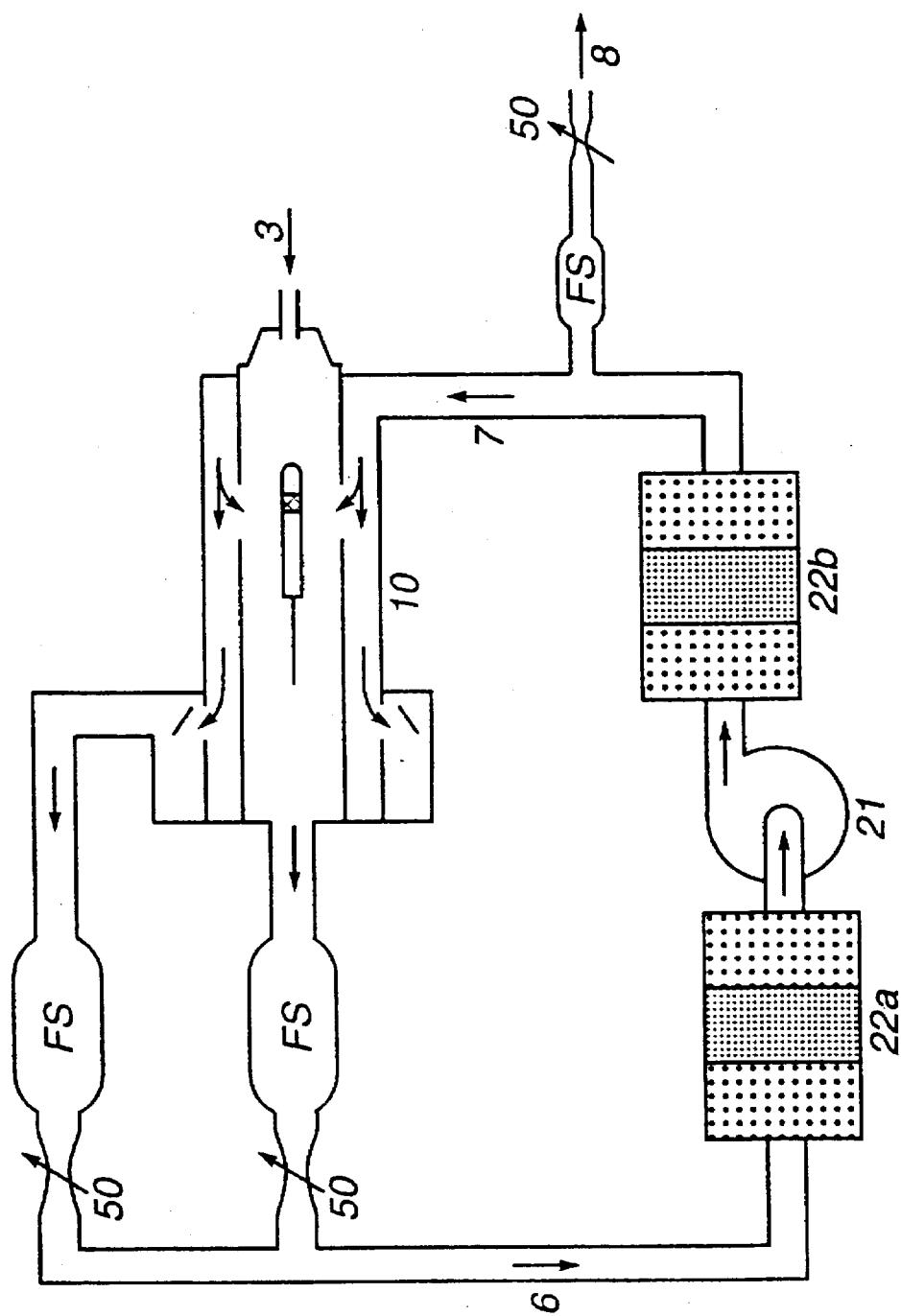

One preferred embodiment of the present invention provides a recirculating filtration system for use with a transportable IMS sensor as shown in FIG. 1. The embodiment shown in FIG. 1 comprises a pump 21 connected with a set of filters 22a and 22b along with a plurality of flow sensors FS and flow adjustment valves 50 to an ion mobility spectrometry (IMS) sensor 10 preferably of the design described in U.S. Pat. No. 5,420,424, the disclosure of which is incorporated herein by reference. The IMS sensor's outlet flow 6 is recirculated back into the IMS sensor 10 as the carrier fluid stream flow 7 described in U.S. Pat. No. 5,420,424. A portion of the IMS sensor's outlet flow 6 equal to the amount of sample flow 3 introduced into the sensor 10 is removed as exhaust 8 from the filtration system to maintain a constant total flow rate through the system as the sample is being taken. The fluid flow rates of the sample 3 and exhaust 8 are typically in the range of 10 to 500 milliliters per minute, while typical carrier fluid stream 7 flow rates are in the range of 2 to 4 liters per minute. Pump 21, preferably of the ASF Model No. 5010 or 7010 Oil-less Diaphragm Pump design, circulates flow through the system. Filters 22a and 22b, which preferably consist of 100 to 500 cubic centimeters (cc) of activated charcoal combined with 200 to 1000 cc of combined type 5A and 13X molecular sieve, clean the outlet flow 6 from the IMS sensor 10 prior to recirculation back into the IMS sensor 10 as the carrier gas 7 described in U.S. Pat. No. 5,420,424. A plurality of flow sensors FS, preferably Honeywell Model AWM3000 series mass flow sensors, are installed to measure flow at various points throughout the system. A plurality of flow adjustment valves 50 are adjusted to initially set the various flow rates in the system to their proper values. These valves 50 are then left at their initial positions during use of the system in making IMS measurements.

The recirculating filtration system displayed in FIG. 1 will permit operation of a portable IMS sensor for the detection of selected atmospheric contaminants in remote locations. However, the accuracy of the sensor's concentration measurement can be adversely affected by charge transfer reactions which occur between the ionizable contaminant of interest and other ionizable species present in the ambient air sample.

Figure 2:
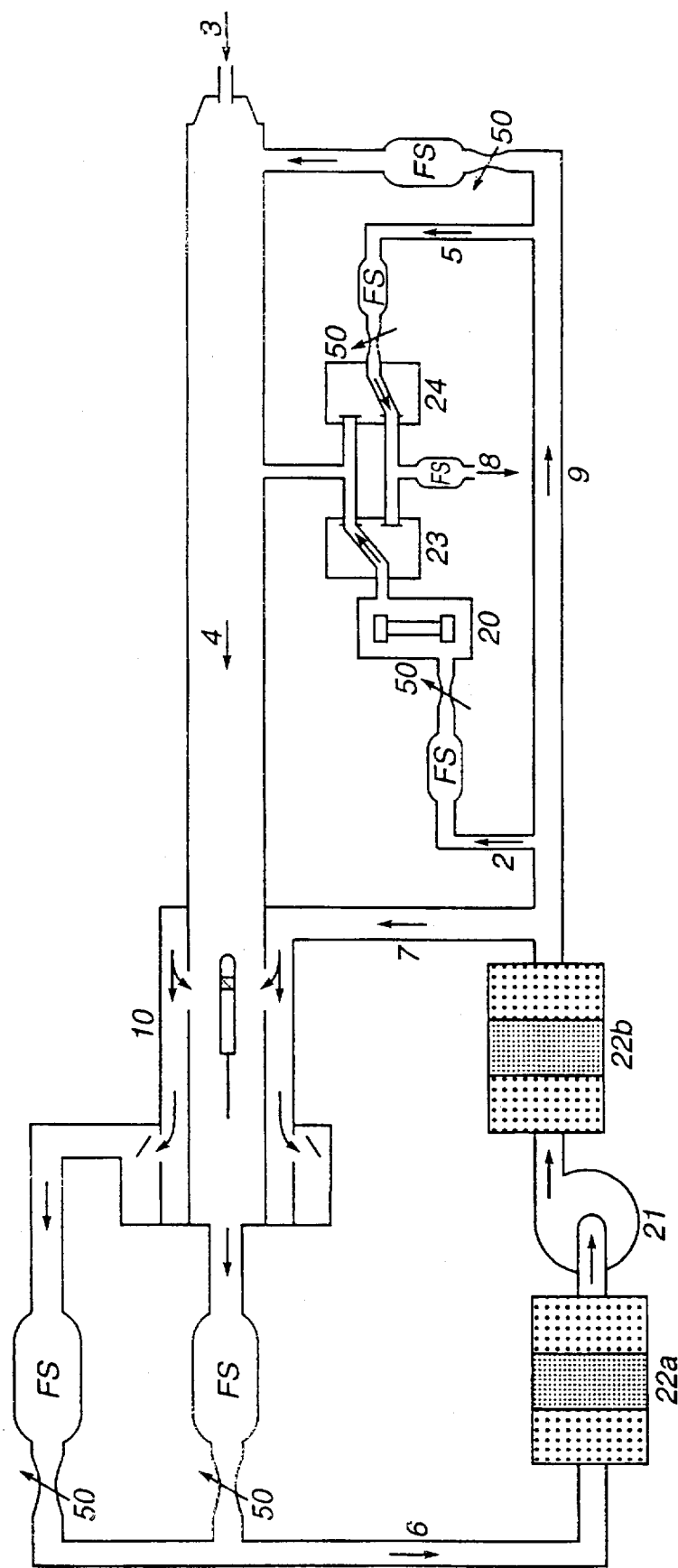

FIG. 2 displays an alternate preferred embodiment of the present invention, which eliminates the effect of charge transfer reactions on the selected ionizable contaminant substance to permit accurate measurement of an unknown concentration level Cs of the selected contaminant in a sample flow 3 in which other substances may coexist. The filtration system is preferably designed for use with the ion mobility spectrometry (IMS) sensor 10 disclosed in U.S. Pat. No. 5,420,424, which is incorporated by reference herein. The filtration system preferably comprises a permeation calibration device 20, a pump 21, a set of filters 22a and 22b, flow sensors FS, two three-port two-way solenoid valves 23 and 24 with interconnecting fluid flow passageways and flow adjustment valves 50. Preferably, a conventional permeation calibration device 20, such as that disclosed in U.S. Pat. Nos. 4,399,942 or 4,715,217, introduces a controlled concentration Cpd of the selected ionizable contaminant substance into the total flow entering the sample stream inlet of the IMS sensor 4 by way of fluid stream 2. Fluid stream 2 passes through permeation calibration device 20 to permit calibration of the IMS sensor 10 response to that expected for the ion concentration introduced and to permit use of the Standard Addition Method in calculating the unknown concentration of the selected contaminant as measured by the IMS sensor 10. Other means of introducing a controlled concentration Cpd of the selected ionizable contaminant into the system that can be used are diffusion vials, diffusion tubes, standards from pressurized calibration cylinders, and other methods such as those disclosed in *Gas Mixtures: Preparation and Control*, Gary O. Nelson (1992).

Preferably, the permeated fluid making up the controlled concentration Cpd consists of a substance such as benzene contained in the permeation calibration device 20 in liquid form and released into the calibration fluid stream 2 in gaseous form, but the filtration system design shown in FIG. 2 can also be adapted for the use of volatile solids or volatile liquids having a boiling point between 40° C. and 125° C., as well as other single phase gases, two-phase solid gas systems or two-phase liquid gas systems desired for use as the permeated fluid. In addition to the permeated fluid, the calibration stream 2 preferably consists of an inert gas or an inert mixture of gases such as that found in dehumidified air which has been filtered through activated charcoal. Typical permeated fluid emission concentrations are between 0.1 and 10 parts per million for calibration fluid stream 2 flow rates in the range of 50 to 200 milliliters per minute. Pump 21, preferably of the ASF Model No. 5010 or 7010 Oil-less Diaphragm Pump design, circulates flow through the system. Filters 22a and 22b, which preferably consist of 100 to 500 cubic centimeters (cc) of activated charcoal combined with 200 to 1000 cc of combined type 5A and 13X molecular sieve, clean the outlet flow 6 from the IMS sensor 10 prior to recirculation back into the IMS sensor 10 as the carrier fluid stream 7 described in U.S. Pat. No. 5,420,424. A first portion of the cleaned outlet flow 6 not introduced into the carrier stream 7 is circulated through the permeation calibration device 20 as the calibration stream 2 and then into the total flow 4 entering the sample stream inlet of the IMS sensor 10. A second portion of the cleaned outlet flow 6 not introduced into the carrier stream 7 is recirculated back into the total flow 4 entering the sample stream inlet of the IMS sensor 10 as the makeup component 5 of the recirculated dilution flow 9 that dilutes the sample 3 to the level necessary for measurement of the unknown concentration. A third portion of the cleaned outlet flow 6 not introduced into the carrier stream 7 is removed as exhaust 8 from the filtration system to maintain a constant total flow volume through the system as the sample is being taken. This exhaust flow 8 is equal to the amount of sample flow 3 introduced into the IMS sensor 10. Sample 3 and exhaust 8 fluid stream flow rates delivered by the system are typically in the range of 10 to 500 milliliters per minute, while typical carrier fluid stream 7 flow rates are in the range of 2 to 4 liters per minute.

A plurality of flow sensors FS, preferably Honeywell Model AWM3000 or AWM5000 series mass flow sensors, are installed to measure flow at various points throughout the system. A plurality of flow adjustment valves 50 are adjusted to initially set the various flow rates in the system to their proper values. These valves 50 are then left at their initial positions during use of the system in making IMS measurements. Valve 23, preferably of the design type LHDA1211111H manufactured by the Lee Company, directs the calibration fluid stream 2 from the permeation calibration device 20 into the total flow 4 entering the sample stream inlet of the IMS sensor 10 or out of the system as required. Valve 24, again preferably of the Lee LHDA1211111H design type, adjusts the makeup component 5 of the recirculated dilution flow 9 such that a constant total IMS sample stream inlet flow 4 is maintained for comparing the controlled concentration of the selected contaminant present in the calibration flow 2 to the unknown concentration to be measured in the sample flow 3. This constant total IMS sample stream inlet flow 4 permits use of the Standard Addition Method in calculating the unknown concentration Cs from the known controlled concentration Cpd. A conventional IMS sensor 10 will work with the system, but the preferred embodiment is designed for use with the IMS sensor disclosed in U.S. Pat. No. 5,420,424.

The measurement of an unknown concentration of the selected contaminant preferably comprises the following steps: (1) combining the controlled contaminant concentration with an unknown concentration of the same contaminant to measure the IMS sensor's response to the combined controlled and unknown concentrations; (2) measuring the IMS sensor's response to only the unknown concentration; and (3) determining this unknown concentration by comparing the measurement in step (1) to the measurement in step (2).

In the first step, valve 23 is positioned to introduce controlled concentration Cpd into the total flow entering the IMS sample stream inlet 4. Valve 24 is positioned to divert makeup flow 5 out of the system as the exhaust 8. The positioning of valve 24 permits the sample flow 3 to be introduced into the total flow entering the IMS sample stream inlet 4. The positioning of valve 24 in concert with the pre-adjustment of the valves 50 causes the sample flow 3 to equal 10% of the total flow entering the IMS sample stream inlet 4. This 10% dilution factor is necessary to dilute the unknown concentration of the selected contaminant in the sample flow 3 to a level that will ensure a linear response of the IMS sensor 10 to changes in the unknown concentration level, but the flow rates preset by the valves 50 could be adjusted to provide for other dilution factors. The IMS sensor 10 measures the combined signal output Stotal produced by ionization of both the controlled concentration Cpd and the unknown concentration Cs of the selected contaminant. Stotal can be characterized by the equation $Stotal = Spd+Ss = A*Cpd+0.1*A*Cs$. A is a constant of proportionality between the electrical signal output S of the IMS 10 and the contaminant concentration C which is generally unknown due to its dependence on charge transfer reactions. The signal output Ss produced by the unknown concentration Cs reflects the 10% dilution factor created by valve 24.

In the second step, valve 23 is repositioned to direct calibration flow 2 out of the system. Valve 24 is repositioned to reinstate maximum makeup flow 5 in combination with the sample flow 3 as the total flow 4 entering the IMS sample stream inlet. The amount of increased makeup flow 5 provided by valve 24 compensates for the amount of calibration flow 2 redirected out of the system to keep the sample flow 3 equal to 10% of the total flow 4 entering the IMS sample stream inlet. The IMS sensor 10 measures the signal output Ss produced by ionization of only the unknown concentration Cs of the selected contaminant. Ss can again be characterized by the equation $Ss=0.1*A*Cs$ as described above.

After performance of the above described measurement sequence, the unknown concentration Cs of the selected contaminant present in the sample flow 3 is calculated by the Standard Addition Method. Since the controlled concentration Cpd is known, the unknown contaminant concentration Cs can be readily obtained by comparing signal output Ss to the combined signal output Stotal. This unknown concentration Cs is calculated by solving the equation $Cs=10*Cpd/(R-1)$ where $R=Stotal/Ss$. Use of the Standard Addition Method to calculate the unknown concentration Cs corrects for the effects of charge transfer reactions on the IMS concentration measurement by eliminating the necessity of arriving at a value for generally unknown proportionality constant A. This calculation can be performed by means of an algorithm run on a computer processor by computer software programmed for this purpose that is stored on a computer-readable storage medium. Other means of calculating the unknown contaminant concentration Cs of the selected contaminant are also possible, such as use of an electronic integrated differential amplifier circuit, an analog or a combined analog and digital comparison circuit comprised of discrete electrical and digital logic components, or other similar circuitry presently in the state of the art.

The alternate preferred embodiment of the present invention also provides a recirculating filtration system which can be used to calibrate the IMS sensor by establishing which ionogram structures result from the presence of a particular analyte in the sample stream. A known concentration of an analyte is introduced into the sample stream. The resulting ionogram is compared to an ionogram recorded with no contaminants present. By comparing these spectra, a correlation can be made between the positions of features in the ionogram and the analyte which gives rise to these features.

The alternate preferred embodiment of the present invention can also be used in calibrating the IMS sensor 10 by introducing only the controlled concentration of the selected contaminant into the IMS. This allows correlating the compensation voltage to generate an ionogram from the measurements taken by the IMS sensor 10.

In the calibration step, valve 23 is positioned to introduce controlled concentration Cpd present in the calibration fluid stream 2 into the total flow entering the IMS sample stream inlet 4. Valves 23 and 24 are positioned to provide maximum makeup flow 5. The lack of exhaust flow 8 out of the system prevents the entry of sample flow 3 into the IMS sample stream inlet flow 4. The total IMS sample stream inlet flow 4 is passed through the IMS sensor 10 to calibrate the IMS sensor 10 output Spd. Spd can be characterized by the equation Spd=A'*Cpd where A' is a constant of proportionality similar to that described above but which has a different value due to a different composition of the total IMS sample stream inlet flow 4. Use of this equation allows comparison of Spd to the output anticipated from ionization of only the controlled concentration Cpd of the selected contaminant. The resulting ionogram is compared to an ionogram recorded with no contaminants present. By comparing these spectra, a correlation can be made between the positions of features in the ionogram and the analyte which gives rise to these features.

While presently preferred embodiments of practicing the invention has been shown and described with particularity in connection with the accompanying drawings, the invention may otherwise be embodied within the scope of the following claims.

What is claimed is:

1. A fluid filtration system for use with an ion mobility spectrometer, comprising:
   A. a pump in communication with both an outlet and a carrier stream inlet of the ion mobility spectrometer for recirculating ion mobility spectrometer outlet fluid flow into the carrier stream inlet;
   B. at least one filter in communication with the pump for removing impurities from the recirculated flow; and
   C. an exhaust in communication with the pump for removing a portion of the recirculated flow from the system, wherein the amount of fluid removed is equal to the amount of fluid entering the sample stream inlet of the ion mobility spectrometer.

2. The fluid filtration system of claim 1, wherein the ion mobility spectrometer is transportable when connected to the filtration system.

3. The fluid filtration system of claim 1, further comprising:
   A. a first filter in communication with the inlet of the pump; and
   B. a second filter in communication with the outlet of the pump; wherein the filters prevent the migration of impurities into the ion mobility spectrometer when the filtration system is not in use.

4. The fluid filtration system of claim 1 for use with an ion mobility spectrometer, wherein the ion mobility spectrometer comprises:
   A. a housing having at least one inlet for communication with a sample media and at least one outlet,
   B. an analyzer positioned within the housing comprising:
      (i) at least first and second longitudinally spaced apart electrodes, the space between the electrodes defining a longitudinal analytical gap, the gap being in communication with a source of carrier gas for flow therethrough,
      (ii) an ionization source juxtaposed with the analytical gap and in communication with the inlet for ionization of sample media,
      (iii) an ion aperture defining an opening between the ionization source and the analytical gap,
      (iv) a third electrode positioned proximate to the ion aperture,
      (v) at least one outlet aperture from the analytical gap remote from the ion aperture,
      (vi) an ion detector for measuring ions from the analytical gap and spaced from the electrodes, and
      (vii) an electrical controller connected to the electrodes for impressing:
         (a) direct current potentials to the first, second and third electrodes, and
         (b) a periodic asymmetrical potential to the first and second electrode, the potentials capable of creating a transverse electric field therebetween during the flow of carrier gas in the analytical gap.

5. A fluid filtration system for use with an ion mobility spectrometer in measuring an unknown concentration level of a selected ionizable substance present in a sample fluid stream in which other substances may coexist, comprising:
   A. a pump in communication with an outlet and carrier and sample stream inlets of the ion mobility spectrometer for recirculating ion mobility spectrometer outlet fluid flow into the carrier and sample stream inlets;
   B. at least one filter in communication with the pump for removing impurities from the recirculated flow;
   C. a plurality of valves in communication with the filters and the sample stream inlet for introducing the sample fluid stream into the sample stream inlet combined with first and second portions of the recirculated flow not directed to the carrier stream inlet, wherein the valves maintain a constant flow rate into the sample stream inlet;
   D. a device in communication with the valves for introducing a controlled concentration level of the selected ionizable substance into the first portion of the recirculated flow not directed to the carrier stream inlet; and
   E. an exhaust in communication with the valves for removing from the system a third portion of the recirculated flow not directed to the carrier stream inlet, wherein the amount of fluid removed equals the amount of fluid in the sample fluid stream.

6. The fluid filtration system of claim 5, wherein the device in communication with the valves for introducing a controlled concentration level of the selected ionizable substance into the first portion of the recirculated flow not directed to the carrier stream inlet is selected from the group consisting of a permeation calibration device, a diffusion vial and a pressurized calibration cylinder.

7. A method of using the fluid filtration system of claim 5 with an ion mobility spectrometer to measure an unknown concentration level of a selected ionizable substance present in a sample fluid stream in which other substances may coexist, comprising the following steps:
   A. introducing a controlled concentration level of the selected ionizable substance into the first portion of the recirculated flow not directed to the carrier stream inlet;
   B. combining the sample fluid stream with both the first and second portions of the recirculated flow not directed to the carrier stream inlet to measure the combined unknown and controlled concentration level;

C. combining the sample fluid stream with the second portion of the recirculated flow not directed to the carrier stream inlet to measure the unknown concentration level;

D. obtaining the unknown concentration by comparing the combined concentration measurement to the unknown concentration measurement.

8. The method of claim 5, wherein the unknown concentration level is obtained by calculating the ratio of the combined concentration measurement to the unknown concentration measurement in accordance with the Standard Addition Method.

9. A method of using the fluid filtration system of claim 6 with an ion mobility spectrometer to measure an unknown concentration level of a selected ionizable substance present in a sample fluid stream in which other substances may coexist, comprising the following steps:

A. introducing a controlled concentration level of the selected ionizable substance into the first portion of the recirculated flow not directed to the carrier stream inlet;

B. combining the sample fluid stream with both the first and second portions of the recirculated flow not directed to the carrier stream inlet to measure the combined unknown and controlled concentration level;

C. combining the sample fluid stream with the second portion of the recirculated flow not directed to the carrier stream inlet to measure the unknown concentration level;

D. obtaining the unknown concentration by comparing the combined concentration measurement to the unknown concentration measurement.

10. The method of claim 6, wherein the unknown concentration level is obtained by calculating the ratio of the combined concentration measurement to the unknown concentration measurement in accordance with the Standard Addition Method.

11. The method of claim 5, wherein the unknown concentration level is calculated by a device selected from the group consisting of a computer processor, an electronic integrated differential amplifier circuit, an analog comparison circuit comprised of discrete electrical components, and a combined analog and digital comparison circuit comprised of discrete electrical and digital logic components.

12. The method of claim 6, wherein the unknown concentration level is calculated by a device selected from the group consisting of computer processor, an electronic integrated differential amplifier circuit, an analog comparison circuit comprised of discrete electrical components, and a combined analog and digital comparison circuit comprised of discrete electrical and digital logic components.

13. A method of using the fluid filtration system of claim 5 to calibrate an ion mobility spectrometer by combining the first and second portions of the recirculated flow not directed to the carrier stream inlet to measure the controlled concentration level.

14. A method of using the fluid filtration system of claim 6 to calibrate an ion mobility spectrometer by combining the first and second portions of the recirculated flow not directed to the carrier stream inlet to measure the controlled concentration level.

15. The fluid filtration system of claim 5, further comprising:

A. a first filter in communication with the inlet of the pump; and

B. a second filter in communication with the outlet of the pump; wherein the filters prevent the migration of impurities into the ion mobility spectrometer when the filtration system is not in use.

16. The fluid filtration system of claim 5, further comprising a plurality of flow sensors for measuring flow at various points throughout the filtration system.

17. The fluid filtration system of claim 5, further comprising a plurality of valves for adjusting the system flow rates.

18. The fluid filtration system of claim 5 for use with an ion mobility spectrometer, wherein the ion mobility spectrometer comprises:

A. a housing having at least one inlet for communication with a sample media and at least one outlet, B. an analyzer positioned within the housing comprising:
  (i) at least first and second longitudinally spaced apart electrodes, the space between the electrodes defining a longitudinal analytical gap, the gap being in communication with a source of carrier gas for flow therethrough,
  (ii) an ionization source juxtaposed with the analytical gap and in communication with the inlet for ionization of sample media,
  (iii) an ion aperture defining an opening between the ionization source and the analytical gap,
  (iv) a third electrode positioned proximate to the ion aperture,
  (v) at least one outlet aperture from the analytical gap remote from the ion aperture,
  (vi) an ion detector for measuring ions from the analytical gap and spaced from the electrodes, and
  (vii) an electrical controller connected to the electrodes for impressing:
    (a) direct current potentials to the first, second and third electrodes, and
    (b) a periodic asymmetrical potential to the first and second electrode, the potentials capable of creating a transverse electric field therebetween during the flow of carrier gas in the analytical gap.

19. The fluid filtration system of claim 5, wherein the selected ionizable substance is selected from the group consisting of a single phase gas, a two-phase solid gas system, and a two-phase liquid gas system.

20. The fluid filtration system of claim 5, wherein the ion mobility spectrometer is transportable when connoted to the filtration system.

* * * * *